(12) United States Patent
Frostegard

(10) Patent No.: US 7,662,577 B2
(45) Date of Patent: Feb. 16, 2010

(54) METHOD OF DIAGNOSING CARDIOVASCULAR DISEASE

(75) Inventor: Johan Frostegard, Nacka (SE)

(73) Assignee: Athera Biotechnologies AB, Stockholm (SE)

( * ) Notice: Subject to any disclaimer, the term of this patent is extended or adjusted under 35 U.S.C. 154(b) by 968 days.

(21) Appl. No.: 10/814,125

(22) Filed: Apr. 1, 2004

(65) Prior Publication Data

US 2004/0185514 A1 Sep. 23, 2004

Related U.S. Application Data

(63) Continuation of application No. 09/720,967, filed as application No. PCT/SE99/01208 on Jul. 2, 1999, now Pat. No. 6,780,605.

(60) Provisional application No. 60/091,741, filed on Jul. 6, 1998.

(30) Foreign Application Priority Data

Jul. 3, 1998 (SE) ..................... 9802402

(51) Int. Cl.
*G01N 33/00* (2006.01)
*G01N 33/53* (2006.01)

(52) U.S. Cl. .............. 435/7.21; 435/7.1; 435/7.9; 435/7.92; 436/501; 436/517; 514/75

(58) Field of Classification Search ............ 435/7.1, 435/7.21, 7.92, 7.9; 436/501, 517; 514/75
See application file for complete search history.

(56) References Cited

U.S. PATENT DOCUMENTS

| | | | |
|---|---|---|---|
| 4,444,879 A | 4/1984 | Foster et al. | |
| 5,731,208 A | 3/1998 | Heinecke | |

FOREIGN PATENT DOCUMENTS

WO    WO 87/05904    * 10/1987

OTHER PUBLICATIONS

Muzya et al. (Immunologiya, 1997, vol. 6, pp. 9-11, Abstract Only).*
Baldo et al, "A specific, sensitive, and high capacity immunoassay for PAF". 1991). 26(12):1136-1139.
Barquinero, Jordi, et al "Antibodies Against Platelet-Activating Factor in Patients With Antiphospholipid Antibodies". Lupus, vol. 3 (1994), pp. 55-58.
Frostegard et al, "Association of Serum Antibodies to Heat-Shock Protein 65 With Borderline Hypertension", Hypertension, 29(1), pp. 40-44, 1997.
Frostegard et al, "Platelet-Activating Factor and Oxidized LDL Induce Immune Activation by a Common Mechanism", Arteriosclerosis, 17(5), pp. 963-968, 1997.
Harris et al, 'Evaluation of the Anti-Cardiolipin Antibody Test: Report of an International Workshop held Apr. 4, 1986:, Clin. Exp Immunol, Apr. 1987, 68(1):215-222.
Hirashima Y et al, "Platelet-activating factor (PAF) and the formation of chronic subdural haematoma. Measurement of plasma PAF levels and anti-PAF immunoglobulin titers". & ACTA Neurochir. (1995) 137(1-2):15-18. (Dialog Information Services, File 154, Medline, Dialog accession No. 08672149, Medline accession No. 96350619).
Karasawa et al, "Radioimmunoassay for platelet activating factor". Lipids. (1991). 26(12):1126-1129.
Lemne et al, "Carotid Intima-Media Thickness and Plaque Borderline Hypertension" Stroke, 26(1); pp. 34-39; 1995.
Ostermann et al, "The degradation of platelet activating factor in serum and its discriminative value in atherosclerotic patients." Thrombosis Research. (1998). 52:529-540.
Boggs, Will, "Chronic H. Pylori Infection Linked to Early Vascular Disease", Society for Vascular Surgery. [online], [retrieved Jul. 5, 2005]. VascularWeb.org. Retrieved from Internet <URL:http://svs.vascularweb.org/_contribution_pages/medical_news_reuters/pag...> reprint of : J AM Coll Cardiol. (2005). 45:1219-1222.
Koh, Kian, et al, "T cell-mediated vascular dysfunction of human allografts results from IFN-γ dysregulation of NO synthase". The Journal of Clinical Investigation. (Sep. 2004). 114(6):846-856.
A. Albertini, et al; "Cost/Benefit and Predictive Value of Radioimmunoassay"; *Symposia of the Giovanni Lorenzini Foundation*; vol. 18, pp. 23-27.

* cited by examiner

*Primary Examiner*—Lisa V Cook
(74) *Attorney, Agent, or Firm*—Fulbright & Jaworski L.L.P.

(57) ABSTRACT

A method of and kit for diagnosing cardiovascular disease in a human involves assessing the presence and/or concentration of antibodies to platelet activating factor (PAF) in a sample of body fluid of the human.

25 Claims, No Drawings

METHOD OF DIAGNOSING CARDIOVASCULAR DISEASE

RELATED APPLICATIONS

The present application is a continuation of parent application Ser. No. 09/720,967 filed Apr. 6, 2001, now U.S. Pat. No. 6,780,605, nationalized on Jan. 3, 2001, which application is the national stage under 35 U.S.C. 371 of PCT/SE99/01208, filed 2 Jul. 1999, itself based on U.S. application 60/091,741 filed Jul. 6, 1998, and claiming priority from Swedish application 9802402-9 filed Jul. 3, 1998.

FIELD OF THE INVENTION

The present invention relates generally to methods for identifying patients who have cardiovascular disease and increased risk of developing atherosclerosis. More particularly, the invention relates to the detection of IgG antibodies to platelet activating factor (PAF) in body fluids of patients. The present inventors have shown that elevated concentrations of antibodies to PAF in body fluids is correlated to borderline hypertension and metabolic syndrome, i.e. early cardiovascular disease, which is connected to increased risk of developing early atherosclerosis.

BACKGROUND OF THE INVENTION

The morbidity and mortality associated with cardiovascular diseases and atherosclerosis in developed countries is higher than that associated with any other disorder. Hypertension is, together with hyperlipidemia, the most prominent risk factor for atherosclerosis. Individuals with borderline hypertension are an example of early cardiovascular disease in general, with endothelial dysfunction and increased risk of atherosclerotic disease, in apparently healthy individuals. Early atherosclerosis manifests itself in the form of cholesterol depositions in the arterial wall. During recent years, it has been convincingly shown that the atherosclerotic process is a chronic inflammation, characterized by presence of activated T cells and monocytes/macrophages. Many of these macrophages have developed into cholesterol-filled foam cells. The deposition is slow and starts at an early age. Clinical symptoms may take years to manifest themselves and are very serious; they include coronary heart disease and stroke. Generally, the disease process will have begun long before these clinical manifestations appear. There are available a number of genetic analysis screening for patients with predeposition for atherosclerosis. But it is desirable to have available a diagnostic technique which provides an early warning of the onset of the deposition. The importance of early detection is stressed by the fact that an effective long-term treatment is possible. The present techniques for diagnosing atherosclerosis depend on measuring cholesterol or triglycerid levels in serum or detection of atheromatous lesions, but by the time of detection, the most effective time for treatment has been passed. U.S. Pat. No. 5,731,208 discloses a screening test for atherosclerosis comprising determining the concentration of p-hydroxyphenylaldehyde-lysine in serum or plasma.

The present inventors have found that elevated concentrations of IgG antibodies to platelet activating factor (PAF) in patients are an indicator of cardiovascular diseases which is often accompanied by early atherosclerosis. More specifically, antibodies to PAF (aPAF) are associated with early vascular disease in the form of both borderline hypertension and the metabolic syndrome, both of which are strong risk factors for later stages of atherosclerosis, which give rise to clinical symptoms.

These results demonstrate that antibodies against PAF represent a novel category of anti-phospholipid antibodies (aPL), which are sensitive to early vascular dysfunction and disease, especially early atherosclerosis and hypertension.

aPL in general, especially against cardiolipin have been shown to predict risk of cardiovascular disease, also in autoimmune diseases like systemic lupus erythematosus (SLE) and our data thus indicate that antibodies against PAF is a novel category of aPL, with a potential as a marker also in other autoimmune conditions in addition to cardiovascular disease and atherosclerosis in general. aPL have been related to both arterial and venous thrombosis, and also to spontaneous abortion. These data indicate that antibodies to PAF were much more strongly associated with spontaneous abortion than aPL, and furthermore, that antibodies to PAF was a novel marker for disease activity in SLE.

Antibodies to PAF are therefore relevant also in these other autoimmune vascular-related diseases.

Also antibodies to PAF-like lipids are relevant in this context, one being lysophosphatidylcholine, where the results indicate a comparable profile as the one obtained by PAF antibodies.

Accordingly, it is a principal object of the present invention to provide a diagnostic method or screening test for early atherosclerosis or cardiovascular changes related to early atherosclerosis. It is yet an other object of the invention to provide a kit for assaying the concentrations of aPAF for diagnosing early atherosclerosis or cardiovascular changes.

"Early atherosclerosis" as used herein refers to the very first stage of atherosclerosis, before the clinical onset of symptoms. "Early cardiovascular disease" as used herein refers to the first stages of cardiovascular disease, as in borderline hypertension and the metabolic syndrome, when atherosclerosis is yet not easy to detect by other methods and has not given rise to disease.

Platelet activating factor (PAF) is a phospholipid inflammatory mediator that is synthesized by a variety of cells, including monocytes and endothelial cells. During oxidation of LDL, PAF-hke Epids are produced. PAF may therefore be of importance in pathological processes in the vascular wall like atherosclerosis and hypertension. In a previous report, the existence of antibodies to PAF (aPAF) were described in individuals with phospholipid antibody syndrome (Barquinero et al., 1994.), but nothing has been reported about possible clinical implications of these antibodies and a putative role in cardiovascular disease.

DISCLOSURE OF THE INVENTION

As mentioned above, we have surprisingly shown that concentration of antibodies to PAF (aPAF) is an effective indicator of early cardiovascular disease. We have found that antibodies to this particular antigen develop in patients well before the clinical onset of atherosclerosis.

In our study we found that concentration of aPAF was 49.3% higher in borderline hypertension men than in normotensive men. When defining aPAF concentrations above mean concentration of control plus two standard deviations (i.e. 0.144+(2×0.109)=0.362 OD405) as positive, 15 men out of 73 were positive in the borderline hypertension group whereas only 3 men out of 73 were positive in the normotensive group. Antibodies to PAF as a marker for early atherosclerosis may be combined with additional and alternative markers for early atherosclerosis to improve the accuracy of the diagnosis, such as determining the concentrations of cholesterol, blood lipids or p-hydroxyphenylaldehyde-lysine.

Antibodies against PAF (aPAF) may be determined using any of the methods and techniques conventional in the art for such determination. Conveniently, such a method may comprise immunoassay e.g. ELISA or RIA. The immunoassay will conveniently use an antigen (PAF) in immobilized form, e.g. on microtitre plates, membranes or beads, to isolate the target aPAF. In a sandwich assay, the bound antigen may be labelled using additional soluble antibody, which may be monoclonal or polyclonal and which may either carry a label or, more conveniently, may itself be labelled subsequently by reaction with a secondary antibody carrying a label. Suitable labels include radionucleides, fluorescent substances, and enzymes.

Alternatively, a competitive binding assay may be used. Conveniently, the components needed to perform the immunoassay will be supplied in kit form. Such a kit would comprise:

a) an antigen capable of binding to aPAF and, optionally;
a labelled sample of antigen to aPAF or a fragment thereof;
said antigen (a) in non-immobilised form;
a labelled secondary antibody specific to said antigen (c)

The body fluid on which the determination is performed may be any body fluid in which aPAF may be located, but conveniently will be or serum or plasma. In some cases it may be convenient to extract the antibodies, or otherwise treat the sample prior to determination.

The invention will now be described in greater detail by reference to the following non-limiting examples:

EXAMPLE 1

Determination of Concentration of PAF Antibodies of Early Atherosclerosis Patients and of Normal Patients In order to investigate the role of aPAF in borderline hypertension (BHT) and early atherosclerosis, we studied a group of 146 middle aged men, where borderline hypertension were compared with age-matched controls. We here report that serum aPAF titers are enhanced in patients with borderline hypertension and metabolic syndrome.

Patients were recruited from a population screening program as previously described (Lemne et al 1995). BHT was defined as diastolic blood pressure (DBP) of 85 to 94 mmHg, and the screening identified 81 men who remained within the range for borderline hypertension during repeated measurements over a three year period. From the same population 80 age matched controls were recruited, whose blood pressure was measured on two occasions a few weeks apart, and was <80 mmHg on both occasions.

Of the 81 men with BHT and the 80 NT controls who agreed to participate, 73 in the BHT and 75 in the NT group completed all procedures of the present study. None of the subjects had any other illnesses or were regularly using any drugs known to influence blood pressure, metabolic or inflammatory variables.

All subjects were investigated according to the same schedule. Both BHT and NT controls were investigated simultaneously when possible and no more than 4 weeks apart. Blood samples for analyses of metabolic and inflammatory variables were taken between 8 and 9:30 a.m., after 8 to 12 hours of fasting. All samples were drawn after 15 minutes of rest in the supine position.

An identical procedure was followed at each occasion during the entire recruitment period. All blood pressure measurements were performed with a mercury sphygmomanometer. The cuff was adjusted according to the circumference of the arm and placed at the level of the heart. Blood pressure was recorded as the mean of two measurements taken after 5 minutes rest in the supine position. Systolic and diastolic blood pressure measurements were defined according to Korotkoff I and V. The same specially trained nurse performed the measurements on all occasions.

The right and left carotid arteries were examined with a duplex scanner (Acuson 128XP/5, Mountain View, Calif., USA) using a 7.0 MHz linear array transducer. The subjects were investigated in the supine position and intima-media (I-M) thickness was determined in the far wall as the distance between the leading edge of the lumen-intima echo and the leading edge of the media-adventitia's echo. Plaque was defined as a localized I-M thickening with a thickness >1 mm and a 100% increase in thickness compared with normal, adjacent wall segments. Plaque occurrence was scored as present or absent. Plaque was screened for in the common, internal and external carotid arteries on: both sides, as described earlier (Lemne et al 1995).

All patients were weighed without other clothing than underwear, using the same scale (Delta 707, SECA, Germany). Length was measured with a special ruler, fixed to the wall. Waist circumference was measured at the level of the umbilicus and the hips were measured at the level of the greatest circumference. Body mass index (BMI) was subsequently calculated as weight in kilograms/(height in meters)$^2$.

IgG antibodies to PAF were determined according to Example 2. PAF (1-0-alkyl-2-acetyl-sn-glycero-3-phosphocholine) was obtained from Sigma, St Louis, USA.

Lipid and lipoprotein levels were determined by a combination of preparative ultracentrifugation followed by lipid analyses in the lipoprotein fractions as previously described (Lemne et al 1995).

Venous blood samples for determination of plasma insulin (Radio-Immuno Assay, Kabi Pharmacia, Sweden) were taken.

Serum immunoglobulins, IgG, IgM and IgA were determined as described (Frostegård et al, Hypertension 1997).

Variables were tested for skewness. For skewed variables non-parametric tests were used for comparisons between the groups (Mann-Whitney U-test), whereas Student's t-test was used for normally distributed variables. Spearman rank correlation coefficients were calculated to estimate interrelations between antibody levels, metabolic variables and blood pressure levels. The significance level was put at $p<0.05$. Values in the text are given as mean±standard deviation (SD) as indicated.

Results

Basic characteristics of the two study groups are presented in Table 1. The mean blood pressure level in the NT group was 125/75(±11/±5) mmHg as compared to 141/89(±10/±2) mmHg in the BHT group. The two groups were well-matched for age. The BHT men had a significantly altered metabolic profile with fasting hyperinsulineamia and dyslipoproteineamia, as previously presented (Table 1). In the BHT group 26% of the subjects had plaque on one or both sides while and the corresponding figure for the NT group was 16% (19 vs 10 subjects, n.s.).

In the material as a whole, the aPAF levels were significantly higher in the BHT group, compared with the NT group (Table II). There was no difference in alysoPAF levels between the BHT and NT group.

There were no significant differences in aPAF levels between individuals with plaque (n=29) compared to individuals without (n=117); data not shown).

If values above 2SD in the control group were defined as positive, 21% in the BHT group and 4% in the NT group had increased aPAF levels. Age did not correlate with antibody levels (data not shown).

To exclude the possibility that differences in antibody levels simply reflected enhanced total antibody levels total IgG was determined. There was no difference between the BHT group and controls (data not shown).

In the material as a whole, and the two groups separately there were no significant correlations between aPAF and BMI, blood pressure levels, or smoking (data not shown).

However, individuals with the metabolic syndrome (defined as having at least two of the following three conditions: BMI>27 kg/m$^2$, insulin levels above the 90$^{th}$ percentile of the normal population, dyslipoproteinemia) had higher aPAF levels than those without (0.222±0.167 versus 0.169±0.106; p=0.0009).

Taken together, individuals with early cardiovascular disease, as in borderline hypertension, had 5 times higher risk of being positive for aPAF than those without.

TABLE I

|  | NT (n = 73) | BHT (n = 73) | p |
|---|---|---|---|
| Waist-hip ratio | 0.90 (±0.05) | 0.92 (±0.05) | 0.022 |
| Current smokers, % | 37 | 32 |  |
| Cholesterol (mmol/l) |  |  |  |
| Plasma | 5.5 (±1.0) | 5.5 (±0.9) |  |
| HDL | 1.27 (±0.27) | 1.16 (±0.28) | 0.016 |
| Triglycerides (mmol/l) |  |  |  |
| Plasma | 1.34 (±0.80) | 1.57 (±0.77) | 0.015 |
| VLDL | 0.85 (±0.69) | 1.0 (±0.68) | 0.029 |
| Insulin (mU/l) | 14.2 (±4.5) | 17.4 (±5.7) | 0.0004 |

Values are given as mean±SD. Group differences were determined by Student's t-test or Mann-Whitney's U-test (skewed variables). HDL=high density lipoprotein, VLDL=very low density lipoprotein.

TABLE II

| Antibody levels to PAF in subjects with or without BHT or metabolic syndrome. | | | |
|---|---|---|---|
|  | NT (n = 73) | BHT (n = 73) | p |
| aPAF, OD405 | 0.144 ± 0.109 | 0.215 ± 0.130 | p = 0.0007 |

Values are given as mean±SD. Group differences were determined by Student's t-test. aPAF=antibody levels to platelet activating factor.

EXAMPLE 2

Method of Determining the Amount of Antibodies to PAF (aPAF) In a Serum Sample

IgG antibodies to PAF and lysoPAF were determined by an enzyme-linked immunosorbent assay (ELISA) essentially as described when phospholipid antibodies including cardiolipin are analyzed (Harris 1986). Titertek® 96-well polyvinylchloride microplates (Flow Laboratories, Costa Mesa, Calif., USA) were coated with 50 μl/well of 50 μg/ml PAF dissolved in ethanol and allowed to dry overnight at 4° C. Blocking was accomplished with 20% ABS-PBS for two hours. 50 μl of serum samples, diluted 1:50 in 20% ABS-PBS were added to each well. Control assay were performed in the absence of PAF.

After 3 washings with PBS the plates were incubated with 50 μl/ml of alkaline phosphatase-conjugated goat anti-human IgG (Sigma A-3150) diluted 1:9000 with PBS at 37° C. for 2 hours. After 3 washings, 100 μl of substrate (phosphatase substrate tablets, Sigma 104; 5 mg in 5 ml diethanolamine buffer, pH 9.8) was added. The plates were incubated in room temperature for 30 minutes and read in an ELISA Multiskan Plus spectrophotometer at 405 nm. Each determination was done in triplicate, The coefficient of variation between triplicate test was less than 5%.

REFERENCES CITED

Lemne C, Jogestrand T, de Faire U. Carotid intima-media thickness and plaque in borderline hypertension. Stroke 1995: 26;34-39.

Frostegård J, Lemne C, Andersson B, Kiessling R and de Faire, U. Association of serum antibodies to heat shock protein 65 with borderline hypertension. Hypertension 1997:29:40-44.

Frostegård J, Huang Y H, Rönnehd J and Schäfer-Elinder L. PAF and oxidized LDL induce immune activation by a common mechanism. Arteriosclerosis, Thrombosis and Vasc Biol. 1997; 17: 963-968.

Barquinero J, Ordi-Ros J, Selva. A, Perez-Peman P, Vilardell M, Khamashta. M. Antibodies against platelet-activating factor in patients with antiphospholipid antibodies. Lupus 1994; 3:55-58.

Harris E N, Gharavi A E, Patel S P, Hughes G R V. Evaluation of the anti-cardiolipin antibody test: report of an international workshop held 4 Apr. 1986. Clin Exp Immunol 1986;68:215-222.

U.S. Pat. No. 5,731,208

What is claimed is:

1. A method for diagnosing early cardiovascular disease comprising (a) contacting a sample of body fluid with phosphocholine and/or a derivative thereof, (b) assessing the presence and/or concentration of antibodies to phosphocholine and/or to said derivative in the sample by measuring antibodies bound to phosphocholine and/or derivative thereof and (c) diagnosing early cardiovascular disease based on the presence and/or concentration of said antibodies to in the sample.

2. The method of claim 1, wherein said early cardiovascular disease comprises atherosclerosis, hypertension or thrombosis.

3. The method of claim 2, wherein measuring comprises an immunoassay.

4. The method of claim 2, wherein measuring comprises an enzyme linked immunosorbent assay.

5. The method of claim 2, wherein measuring comprises a radioimmunoassay.

6. The method of claim 2, wherein said body fluid is serum prepared from a blood sample.

7. The method of claim 2, wherein said body fluid is plasma prepared from a blood sample.

8. The method of claim 1, wherein measuring comprises an immunoassay.

9. The method of claim 1, wherein measuring comprises an enzyme linked immunosorbent assay.

10. The method of claim 1, wherein measuring comprises a radioimmunoassay.

11. The method of claim 1, wherein said body fluid is serum prepared from a blood sample.

12. The method of claim 1, wherein said body fluid is plasma prepared from a blood sample.

13. The method of claim 1, wherein said body fluid is a human blood sample or fraction thereof, and said measuring comprises an immunoassay.

14. The method of claim 2, wherein said derivative is lyphosphatidyleholine.

15. The method of claim 1, wherein said derivative is lysophosphatidyleholine.

16. The method of claim 3, wherein said derivative is lysophosphatidyicholine.

17. The method of claim 4, wherein said derivative is lysophosphatidyicholine.

18. The method of claim 5, wherein said derivative is lysophosphatidyicholine.

19. The method of claim 6, wherein said derivative is lysophosphatidyicholine.

20. The method of claim 1, wherein said body fluid is contacted with phosphochline.

21. The method of claim 2, wherein said body fluid is contacted with phosphochline.

22. The method of claim 3, wherein said body fluid is contacted with phosphochline.

23. The method of claim 4, wherein said body fluid is contacted with phosphochline.

24. The method of claim 5, wherein said body fluid is contacted with phosphochline.

25. The method of claim 6, wherein said body fluid is contacted with phosphochline.

* * * * *

UNITED STATES PATENT AND TRADEMARK OFFICE
CERTIFICATE OF CORRECTION

PATENT NO. : 7,662,577 B2
APPLICATION NO. : 10/814125
DATED : February 16, 2010
INVENTOR(S) : Johan Frostegard It is certified that error appears in the above-identified patent and that said Letters Patent is hereby corrected as shown below:

In claim 1, column 6, line 44, insert a --,-- after "thereof".

In claim 1, column 6, line 46, delete "antibodies to in" and insert --antibodies in-- therefor.

In claim 14, column 7, line 7, delete "lyphosphatidyleholine" and insert --lysophosphatidylcholine-- therefor.

In claim 15, column 7, line 9, delete "lysophosphatidyleholine" and insert --lysophosphatidylcholine-- therefor.

In claim 16, column 7, line 11, delete "lysophosphatidyicholine" and insert --lysophosphatidylcholine-- therefor.

In claim 17, column 7, line 13, delete "lysophosphatidyicholine" and insert --lysophosphatidylcholine-- therefor.

In claim 18, column 7, line 15, delete "lysophosphatidyicholine" and insert --lysophosphatidylcholine-- therefor.

In claim 19, column 8, line 2, delete "lysophosphatidyicholine" and insert --lysophosphatidylcholine-- therefor.

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,662,577 B2 | Page 1 of 1 |
| APPLICATION NO. | : 10/814125 | |
| DATED | : February 16, 2010 | |
| INVENTOR(S) | : Johan Frostegard | |

It is certified that error appears in the above-identified patent and that said Letters Patent is hereby corrected as shown below:

Title page (*) Notice

Delete "by 968 days" – and insert --by 904 days--

Signed and Sealed this

Twenty-fourth Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,662,577 B2  Page 1 of 1
APPLICATION NO. : 10/814125
DATED : February 16, 2010
INVENTOR(S) : Johan Frostegard It is certified that error appears in the above-identified patent and that said Letters Patent is hereby corrected as shown below:

In title page, item (*) Notice, line 4, insert
--This patent is subject to a terminal disclaimer.--.

Signed and Sealed this

Second Day of November, 2010

David J. Kappos
*Director of the United States Patent and Trademark Office*